United States Patent
Shalaby

(10) Patent No.: US 8,865,205 B2
(45) Date of Patent: *Oct. 21, 2014

(54) BIOSWELLABLE SUTURES

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/229,142

(22) Filed: Aug. 20, 2008

(65) Prior Publication Data

US 2009/0017083 A1 Jan. 15, 2009

Related U.S. Application Data

(63) Continuation-in-part of application No. 11/596,545, filed on Nov. 15, 2006, now abandoned, which is a continuation-in-part of application No. 11/453,207, filed as application No. PCT/US2006/022971 on Jun. 14, 2006.

(60) Provisional application No. 60/741,329, filed on Dec. 1, 2005, provisional application No. 60/690,751, filed on Jun. 15, 2005.

(51) Int. Cl.
| | | |
|---|---|---|
| *A61K 9/14* | (2006.01) | |
| *A61K 9/70* | (2006.01) | |
| *A61L 27/34* | (2006.01) | |
| *A61L 17/14* | (2006.01) | |
| *A61L 29/08* | (2006.01) | |
| *A61B 17/06* | (2006.01) | |
| *A61B 17/00* | (2006.01) | |

(52) U.S. Cl.
CPC ........... *A61B 17/06166* (2013.01); *A61L 27/34* (2013.01); *A61L 17/145* (2013.01); *A61L 29/085* (2013.01); *A61B 2017/00889* (2013.01)
USPC .......................................... 424/443; 424/486

(58) Field of Classification Search
None
See application file for complete search history.

(56) References Cited

U.S. PATENT DOCUMENTS

| | | | | |
|---|---|---|---|---|
| 4,624,256 | A | * | 11/1986 | Messier et al. ................. 606/230 |
| 5,123,912 | A | * | 6/1992 | Kaplan et al. .................. 606/230 |
| 5,320,624 | A | * | 6/1994 | Kaplan et al. .................... 606/77 |
| 5,543,158 | A | * | 8/1996 | Gref et al. ...................... 424/501 |
| 6,136,018 | A | * | 10/2000 | Roby et al. ..................... 606/228 |
| 6,498,229 | B1 | * | 12/2002 | Shalaby ......................... 528/302 |
| 2003/0162940 | A1 | * | 8/2003 | Shalaby ......................... 528/425 |
| 2005/0171299 | A1 | * | 8/2005 | Shalaby ......................... 525/437 |
| 2006/0286143 | A1 | | 12/2006 | Shalaby |
| 2007/0275034 | A1 | | 11/2007 | Shalaby |
| 2008/0089840 | A1 | | 4/2008 | Shalaby |

FOREIGN PATENT DOCUMENTS

WO  WO 2006/138300  * 12/2006

OTHER PUBLICATIONS

Miller et al., Surgery, 10 (2), 156, 1987.
Cai et al., Synthesis and properties of ABA-type triblock copolymers of poly(glycolide-o-caprolactone) (A) and poly (ethylene glycol (B), Polymer 43, p. 3585-3591, 2002.

* cited by examiner

*Primary Examiner* — Brian-Yong Kwon
*Assistant Examiner* — Lyndsey Beckhardt

(57) ABSTRACT

Swellable, coated sutures have a swellable polymeric coating and a fibrous component, wherein the coating is formed of an absorbable or non-absorbable polymer, while the fibrous component is formed of a synthetic absorbable or non-absorbable monofilament yarn, synthetic absorbable or non-absorbable braided multifilament yarn, braided silk multifilament yarn or combinations thereof. In certain instances, the coating is used as a carrier for the controlled delivery of different types of bioactive agents, including those having antimicrobial, anti-inflammatory, anesthetic, tissue growth-promoting, and antineoplastic activities.

15 Claims, No Drawings

US 8,865,205 B2

BIOSWELLABLE SUTURES

The present application is a continuation in part of U.S. application Ser. No. 11/596,545, filed on Nov. 15, 2006, which is a continuation in part of U.S. application Ser. No. 11/453,207 filed on Jun. 14, 2006, is a National Stage entry of PCT/US06/22,971, filed on Jun. 14, 2006, which claims the benefits of prior provisional application No. 60/741,329, filed on Dec. 1, 2005, and provisional application No. 60/690,751, filed on Jun. 15, 2005.

FIELD OF THE INVENTION

This invention is directed toward coated, bioswellable surgical sutures having a swellable absorbable or non-absorbable coating on a monofilament yarn, braided multifilament yarn, or combinations thereof, wherein the yarns are formed of at least one absorbable polymer, one non-absorbable polymer, or a combination thereof. The swelling of the sutures is manifested through the hydroswelling of the fibrous and/or coating components. The coating contains at least one bioactive agent to impart anti-inflammatory, antineoplastic, anesthetic, tissue growth-promoting, antiviral, and/or antimicrobial activities.

BACKGROUND OF THE INVENTION

Prior art of relevance to the present invention includes U.S. patent application Ser. No. 11/453,207, directed to absorbable, essentially non-absorbable and non-absorbable, crystalline, amphiphilic block/graft compositions having an inherent viscosity of at least 0.5 dL/g, and a heat of fusion of at least 10 J/g, that undergo swelling in the biological environments due to a water uptake of at least 10 percent of the original mass. These compositions were designed for use in swellable surgical sutures, coatings, and carriers for the delivery of bioactive agents. Related to this was a subsequent disclosure (U.S. patent application Ser. No. 11/820,849) which dealt with biomedical and tissue engineering devices (such as surgical sutures and microporous scaffolds, respectively), which undergo swelling and increase in dimensions when placed in aqueous environments, such as living tissues, that are produced by the melt-spinning or electrostatic spinning as strong monofilament and multifilament yarns or microfibrous fabrics, respectively. It was also disclosed that such devices are formed from especially high molecular weight crystalline polyether-esters having a minimum inherent viscosity of 0.8 dL/g, wherein the polyether-esters are made by grafting a polyester segment or block to a polyether glycol component having a minimum molecular weight of 11 kDa with at least one cyclic monomer.

The parent application to this invention (U.S. patent application Ser. No. 11/596,545 and PCT/U.S. application Ser. No. 06/22,971) is directed to bioswellable sutures in the forms of absorbable monofilaments of an amphiphilic copolyester, an absorbable multifilament braid, a non-absorbable multifilament braid with an absorbable monofilament core of an amphiphilic copolymer and a non-absorbable multifilament braid molecularly integrated with an outer sheath that is highly hydrophilic.

Analysis of the prior art discussed above and related art did not reveal any teaching dealing with (1) coated sutures that are swellable due to, at least in part, a swellable polymeric coating thereon; (2) swellable coating on swellable sutures where the fibrous component of the suture comprises absorbable and non-absorbable yarns; and (3) swellable coating on non-absorbable sutures or silk. Similarly, swellable sutures comprising a swellable and non-swellable fibrous component could not be found in the prior art. Failure of the prior art to deal with or make it obvious to conceive these unreported, novel features of swellable, coated sutures provided an incentive to pursue the study subject of the instant invention.

SUMMARY OF THE INVENTION

A major aspect of this invention deals with a bioswellable suture comprising a bioswellable coating which comprises a crystalline, aliphatic, segmented/block polyether-ester representing 0.1 to 15 percent by weight of the total suture weight; wherein the bioswellable coating exhibits an inherent viscosity of less than 0.7 dL/g and preferably less than 0.5 dL/g and more preferably less than 0.2 dL/g, heat of fusion of less than 70 J/g and preferably less than 50 J/g and more preferably less than 25 J/g and most preferably less than 15 J/g and comprising polyethylene glycol grafted with a mixture comprising about 85-99 percent by mole of ε-caprolactone and about 1-15 percent by mole of at least one additional monomer selected from the group consisting of glycolide, p-dioxanone, lactide, and a morpholinedione; and wherein the grafted aliphatic polyether glycol is a polyethylene glycol having a molecular weight of 0.4 to 15 kDa, and further wherein the (1) underlying suture comprises an absorbable monofilament yarn comprising a polymer made by the ring-opening polymerization of at least one cyclic monomer selected from the group consisting of glycolide, l-lactide, ε-caprolactone, trimethylene carbonate, p-dioxanone, 1,5-dioxepan-2-one, and a morpholinedione; (2) underlying suture comprises a swellable, absorbable monofilament yarn comprising a polymer made by end grafting an aliphatic polyether glycol with at least one cyclic monomer selected from the group consisting of glycolide, l-lactide, ε-caprolactone, trimethylene carbonate, p-dioxanone, 1,5-dioxepan-2-one, and a morpholinedione; (3) the underlying suture comprises an absorbable, braided multifilament yarn comprising at least one type of polymer made by end-grafting a polyether glycol with at least one monomer selected from the group consisting of glycolide, l-lactide, ε-caprolactone, trimethylene carbonate, p-dioxanone, 1,5-dioxepan-2-one, and a morpholinedione; or (4) underlying suture comprises a braided multifilament comprising a multifilament silk yarn. Additionally, the polyether glycol used for preparing the underlying suture comprises a polyethylene glycol having a molecular weight of 1 to 35 kDa.

A specific aspect of this invention deals with a bioswellable suture having a bioswellable coating thereon, the coating comprising a crystalline, aliphatic, segmented/block polyether-ester and comprising from about 0.1 to about 15 percent by weight of the total suture weight, wherein the bioswellable coating comprises an aliphatic polyether glycol grafted with a mixture of from about 85 to about 99 percent by mole of ε-caprolactone and from about 15 to about 1 percent by mole of at least one additional monomer selected from the group consisting of glycolide, p-dioxanone, lactide, and a morpholinedione, and wherein the coating exhibits an inherent viscosity of less than about 0.7 dL/g and preferably less than 0.5 dL/g and more preferably less than 0.2 dL/g, and heat of fusion of less than about 70 J/g and preferably less than 50 J/g and more preferably less than 25 J/g and most preferably less than 15 J/g; and wherein the grafted aliphatic polyether glycol is a polyethylene glycol having a molecular weight of 0.4 to 15 kDa and further wherein the underlying suture comprises an absorbable, braided multifilament yarn comprising at least one type of polymer made by the ring-opening polymerization of at least one monomer selected from the group consisting of glycolide, l-lactide, ε-caprolactone, trimethylene carbonate, p-dioxanone, 1,5-dioxepan-2-one, and a morpholinedione. Alternatively, the underlying suture comprises an absorbable, braided multifilament yarn made by end-grafting an aliphatic polyethylene glycol, having a molecular weight of 1 to 35 kDa, with at least one cyclic monomer selected from the group consisting of glycolide, l-lactide, ε-caprolactone, trimethylene carbonate, p-dioxanone, 1,5-dioxepan-2-one, and a morpholinedione.

Another major aspect of this invention deals with a bioswellable suture having a bioswellable coating thereon, the coating comprising a crystalline, aliphatic, segmented/block polyether-ester and comprising from about 0.1 to about 15 percent by weight of the total suture weight, wherein the bioswellable coating comprises a segmented/block copolyether-ester comprising a polyethylene glycol segment/block and an aliphatic polyester segment/block of an aliphatic polyester selected from the group consisting of poly-ε-caprolactone, polytetramethylene adipate, polyethylene sebacate, polyhexamethylene succinate, and polyoctamethylene oxalate, and wherein the coating exhibits an inherent viscosity of less than about 0.7 dL/g and a heat of fusion of less than about 70 J/g, but preferably less than 0.5 dL/g and 25 J/g and more preferably, less than 0.2 dL/g and 15 J/g, and wherein the (1) underlying suture is selected from the group consisting of a polypropylene monofilament, braided multifilament silk yarn, braided multifilament polyethylene terephthalate yarn, braided multifilament Nylon 66 yarn, braided multifilament polytetramethylene terephthalate yarn, monofilament of poly (tetramethylene terephthalate-b-polytetramethylene terephthalate), braided multifilament yarn of ultrahigh molecular weight polyethylene, and composite braided multifilament yarn comprising ultrahigh molecular weight polyethylene and an absorbable polyester, or (2) underlying suture comprises a non-absorbable, segmented/block polyether-ester comprising polyethylene glycol-based segments/blocks and at least one aliphatic segment/block selected from the group consisting of tetramethylene terephthalate, trimethylene terephthalate, and ethylene terephthalate sequences.

A clinically important aspect of this invention deals with a bioswellable suture having a bioswellable coating thereon, the coating comprising a crystalline, aliphatic, segmented/block polyether-ester and comprising from about 0.1 to about 15 percent by weight of the total suture weight, wherein the bioswellable coating comprises an aliphatic polyether glycol grafted with a mixture of from about 85 to about 99 percent by mole of ε-caprolactone and from about 15 to about 1 percent by mole of at least one additional monomer selected from the group consisting of glycolide, p-dioxanone, lactide, and a morpholinedione, and wherein the coating exhibits an inherent viscosity of less than about 0.7 dL/g and preferably less than about 0.5 dL/g and more preferably less than 0.2 dL/g, and heat of fusion of less than about 70 J/g and preferably less than about 50 J/g and more preferably less than about 25 J/g and most preferably less than about 15 J/g, and wherein the grafted aliphatic polyether glycol is a polyethylene glycol having a molecular weight of 0.4 to 15 kDa, and further wherein the coating comprises at least one bioactive agent selected from the group consisting antimicrobial agents, anti-inflammatory agents, antiviral agents, antineoplastic agents, anesthetic agents, and tissue growth-promoting agents.

Another clinically important aspect of this invention deals with a bioswellable suture having a bioswellable coating thereon, the coating comprising a crystalline, aliphatic, segmented/block polyether-ester and comprising from about 0.1 to about 15 percent by weight of the total suture weight, wherein the bioswellable coating comprises a segmented/block copolyether-ester comprising a polyethylene glycol segment/block and an aliphatic polyester segment/block of an aliphatic polyester selected from the group consisting of poly-ε-caprolactone, polytetramethylene adipate, polyethylene sebacate, polyhexamethylene succinate, and polyoctamethylene oxalate, and wherein the coating exhibits an inherent viscosity of less than about 0.7 dL/g and preferably less than about 0.5 dL/g and more preferably less than 0.2 dL/g, and a heat of fusion of less than about 70 J/g and preferably less than about 50 J/g and more preferably less than about 25 J/g and most preferably less than about 15 J/g, and wherein the coating comprises at least one bioactive agent selected from the group consisting of antimicrobial agents, anti-inflammatory agents, antiviral agents, antineoplastic agents, anesthetic agents, and tissue growth-promoting agents.

DETAILED DESCRIPTION OF PREFERRED EMBODIMENTS

The present invention is directed to hydroswellable, coated sutures that undergo swelling in aqueous environments, such as in living tissues, wherein the fibrous components of the sutures and/or their coatings are responsible for the ability to absorb water and undergo swelling. The chemical structures of these coatings are tailored to produce polymeric chains with highly hydrophilic, water-absorbing polyoxyethylene segments or blocks linked covalently to relatively hydrophobic polyester chains. The latter can be further designed to have modulated absorption profiles depending upon the sought in vivo performance of the suture. Apart from their ability to undergo water-induced swelling, or hydroswelling, the molecular weight and thermal properties of the coatings are tailored to increase the surface lubricity of the sutures and reduce their frictional coefficient. This is achieved by having preferably low-melting and low- to moderate-crystallinity segments in the polymeric chains. In addition to the lubricious nature and ability of the coating materials to undergo swelling, the amphiphilic nature of their constituent polymeric chains displays differing degrees of surface activity typically encountered in nonionic surfactants. This, in turn, increases the effectiveness of the coatings in imparting surface lubricity in wet environments. When used as a suture coating, not only the dry tie-down characteristics are generally improved, but also the friction force decreases, further, upon exposure to an aqueous medium. Another important feature associated with the amphiphilic, swellable coating is the ability to control the fraction of the hydrophobic and hydrophobic components to allow the use of the coatings as vehicles for the controlled release of bioactive agents of variable affinity to these components. This and controlling the extent and rate of swelling of these coatings provide an extensive opportunity to use the coatings as effective carriers for a broad spectrum of bioactive agents to allow their release as per any desired profile.

Another primary aspect of this invention deals with the broad spectrum of the type of fibrous components of the suture, which can be coated with the swellable coating polymer. Thus, the fibrous components can be in the form of (1) an absorbable or non-absorbable monofilament; (2) an absorbable or non-absorbable braided multifilament; (3) a braided silk multifilament; (4) a composite suture braid comprising an absorbable and non-absorbable component; (5) a swellable, absorbable or non-absorbable monofilament; (6) a swellable, absorbable or non-absorbable braid; (6) a composite braid of swellable and practically non-swellable multifilament; and (7) a composite braid of swellable and non-swellable components.

Further illustrations of the present invention are provided by the following examples:

EXAMPLE 1

Synthesis and Characterization of a Polyether-ester by Grafting Polyethylene Glycol with 99/1 ε-Caprolactone/Glycolide as a Typical Swellable Coating, C-I Predried polyethylene glycol (35 g) having a molecular weight of 1000 Da was mixed in a pre-dried polymerization reactor (equipped for mechanical stirring and outlets for applying vacuum, introducing nitrogen, and introducing components of the charge) with ε-caprolactone (565 mmole, 64.41 g) and glycolide (5.1 mmole, 0.59 g) and heated under nitrogen to 110° C. The polymerization charge was stirred to produce uniform liquid. To this was added a solution of stannous octanoate in toluene (1 mL of 0.228 molar solution, 0.228 mmole) to provide a monomer/catalyst ratio of 2500/1. The reactants were heated while stirring to 160° C. and maintained at this temperature until practically complete monomer conversion (about 15 hours) as determined by gel-permeation chromatography (GPC). At the conclusion of the polymerization, the polymer was cooled to room temperature, isolated and analyzed for identity (by infrared and NMR), thermal properties (DSC), molecular weight (viscometry and GPC). The differential scanning calorimetry data indicated a $T_{m1}=29°$ C. and $T_{m2}=46°$ C., and an overall heat of fusion of 44 J/g. Viscosity and molecular weight data can be summarized as follows: inherent viscosity (in $CHCl_3$)=0.14 dL/g; $M_w$=7 kDa.

EXAMPLE 2

Synthesis and Characterization of Polyether-ester by Grafting Polyethylene Glycol with 95/5 ε-Caprolactone/Glycolide as a Typical Absorbable, Swellable Coating, C-II Coating copolymer C-II was prepared and characterized under conditions similar to those used in Example 1 with the exception of using 16.25 g of the polyethylene glycol having a molecular weight of 1000 Da and a mixture of ε-caprolactone (541 mmole, 61.7 g) and glycolide (28.4 mmole, 3.3 g) instead of ε-caprolactone alone. Analytical data for C-II can be summarized as follows: $T_m$=45° C.; $\Delta H_f$=62 J/g; $M_n$=37 kDa; $M_w$=16 kDa.

EXAMPLE 3

Coating and Testing of a Braided Multifilament Silk Braid with Swellable Coating C-I from Example 1

A braided silk suture having a diameter of 0.34 mm was coated with a 18 percent acetone solution of C-I polymer (from Example 1) using a standard dipping technique at room temperature. The coated suture was dried to a constant weight to determine a coating add-on of 10.3 percent. The coated suture was tested against the uncoated suture and indicated: (a) an improvement of the dry tie-down characteristics which improved further when tested after wetting in an aqueous medium—the decrease in the friction force was more pronounced in the case of the wet suture; (b) a decrease in the friction force using a mechanical simulation of tie-down under typical dry and wet surgical applications; and (c) increase in cross-sectional area upon soaking in saline for one hour.

EXAMPLE 4

Coating and Testing of a Braided Multifilament Yarn of Absorbable Glycolide copolymer with Swellable Coating C-II from Example 2

A practically non-swellable braided suture made of 95/5 (molar) glycolide/ε-caprolactone, having a diameter of 0.33 mm, was coated with a 15 percent acetone solution of C-II polymer (from Example 2) using a standard dipping technique at room temperature. The coated sutures were dried to a constant weight to determine a coating add-on of 4.3 percent. The coated suture was tested against the uncoated suture and indicated: (a) an improvement of dry tie-down characteristics which improved further when tested after wetting in an aqueous medium; (b) a decrease in the friction force using a mechanical simulation of tie-down under typical dry and wet surgical applications—the decrease in the friction force was more pronounced in the case of the wet suture; and (c) increase in cross-sectional area upon soaking in saline for one hour.

EXAMPLE 5

Coating and Testing of a Swellable Braided Multifilament Yarn of an Absorbable Polyether-ester Using Coating C-II from Example 2

A swellable braided suture made of polyethylene glycol end-grafted with a mixture of 70/30 (molar) glycolide/caprolactone, having a diameter of 0.31 mm, was coated with a 15 percent acetone solution of C-II polymer (from Example 2) using a standard dipping technique at room temperature. The coated sutures were dried to a constant weight to determine a coating add-on of 3 percent. The coated suture was tested against the uncoated suture and indicated: (a) an improvement of dry tie-down characteristics which improved further when tested after wetting in an aqueous medium; (b) a decrease in the friction force using a mechanical simulation of tie-down under typical dry and wet surgical applications—the decrease in the friction force was more pronounced in the case of the wet suture; and (c) increase in cross-sectional area upon soaking in saline for one hour.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A bioswellable suture having an underlying suture and a bioswellable coating thereon, wherein the bioswellable coating comprises an aliphatic polyether glycol grafted with a mixture of cyclic monomers comprising from about 85 to about 99 percent by mole of ε-caprolactone and from about 15 to about 1 percent by mole of at least one additional monomer selected from the group consisting of glycolide, p-dioxanone, lactide, and a morpholinedione, to form a triblock polymer with a central block derived from the aliphatic polyether glycol and terminal blocks derived from cyclic monomers, wherein the coating exhibits an inherent viscosity of less than about 0.7 dL/g and heat of fusion of less than about 70 J/g, and wherein the coating comprises from about 0.1 to about 15 percent by weight of the total suture weight, the coated suture exhibiting an increase in cross-sectional area upon soaking in saline for one hour; and the grafted aliphatic polyether glycol is a polyethylene glycol having a molecular weight of 0.4 to 15 kDa.

2. A bioswellable suture as in claim 1 wherein the underlying suture comprises an absorbable monofilament yarn comprising a polymer made by the ring-opening polymerization of at least one cyclic monomer selected from the group consisting of glycolide, l-lactide, ϵ-caprolactone, trimethylene carbonate, p-dioxanone, 1,5-dioxepan-2-one, and a morpholinedione.

3. A bioswellable suture as in claim 1 wherein the underlying suture comprises a swellable, absorbable monofilament yarn comprising a polymer made by end grafting an aliphatic polyether glycol with at least one cyclic monomer selected from the group consisting of glycolide, l-lactide, ϵ-caprolactone, trimethylene carbonate, p-dioxanone, 1,5-dioxepan-2-one, and a morpholinedione.

4. A bioswellable suture as in claim 1 wherein the underlying suture comprises an absorbable, braided multifilament yarn comprising at least one type of polymer made by the ring-opening polymerization of at least one monomer selected from the group consisting of glycolide, l-lactide, ϵ-caprolactone, trimethylene carbonate, p-dioxanone, 1,5-dioxepan-2-one, and a morpholinedione.

5. A bioswellable suture as in claim 4 wherein the absorbable, braided multifilament yarn further comprises at least one additional copolymer made by end-grafting an aliphatic polyether glycol with at least one cycle monomer selected from the group consisting of glycolide, l-lactide, ϵ-caprolactone, trimethylene carbonate, p-dioxanone, 1,5-dioxepan-2-one, and a morpholinedione.

6. A bioswellable suture as in claim 1 wherein the underlying suture comprises an absorbable, braided multifilament yarn comprising at least one type of polymer made by end-grafting a polyether glycol with at least one monomer selected from the group consisting of glycolide, l-lactide, ϵ-caprolactone, trimethylene carbonate, p-dioxanone, 1,5-dioxepan-2-one, and a morpholinedione.

7. A bioswellable suture as in claim 6 wherein the polyether glycol in the yarn comprises a polyethylene glycol having a molecular weight of 1 to 35 kDa.

8. A bioswellable suture as in claim 1 wherein the underlying suture comprises a braided multifilament comprising a multi-filament silk yarn.

9. A bioswellable suture as in claim 1 wherein the coating comprises at least one bioactive agent selected from the group consisting antimicrobial agents, anti-inflammatory agents, antiviral agents, antineoplastic agents, anesthetic agents, and tissue growth-promoting agents.

10. A bioswellable suture as in claim 1 wherein the bioswellable coating comprises polyethylene glycol grafted with a mixture of ϵ-caprolactone and glycolide.

11. A bioswellable suture as in claim 10 wherein the bioswellable coating comprises polyethylene glycol grafted with a mixture of 99/1 mole % ϵ-caprolactone and glycolide.

12. A bioswellable suture as in claim 10 wherein the bioswellable coating comprises polyethylene glycol grafted with a mixture of 95/5 mole % ϵ-caprolactone/glycolide.

13. A bioswellable suture as in claim 12 wherein the underlying suture comprises a braided multifilament made of 95/5 (molar) glycolide/ϵ-caprolactone.

14. A bioswellable suture as in claim 12 wherein the underlying suture comprises a braided multifilament made of 70/30 (molar) glycolide/ϵ-caprolactone.

15. A bioswellable suture as in claim 1 wherein the underlying suture comprises a braided multifilament made of 95/5 (molar) glycolide/ϵ-caprolactone.

* * * * *